United States Patent [19]

Brion et al.

[11] Patent Number: 5,550,143
[45] Date of Patent: Aug. 27, 1996

[54] HETEROCYCLIC COMPOUNDS

[75] Inventors: Jean-Daniel Brion, St-Leu-La-Foret; Anne-Marie Chollet, Viroflay; Luc Demuynck, Orleans; Lucy De Montarby, Courbevoie; Yves Rolland, Vanves; Jacqueline Bonnet, Paris, all of France; Pietro Ghezzi, Milan, Italy; Armel Fradin, Neuilly-Sur-Seine, France

[73] Assignee: Adir et Compagnie, Courbevoie, France

[21] Appl. No.: 226,633

[22] Filed: Apr. 12, 1994

Related U.S. Application Data

[62] Division of Ser. No. 66,524, May 24, 1993, abandoned.

[30] Foreign Application Priority Data

May 25, 1992 [FR] France .................................. 92 06353

[51] Int. Cl.⁶ ........................ A61K 31/425; C07D 277/68
[52] U.S. Cl. .......................... 514/367; 548/159; 548/170; 548/173
[58] Field of Search ...................... 548/170, 173, 548/159; 514/367

[56] References Cited

U.S. PATENT DOCUMENTS

| | | | |
|---|---|---|---|
| 2,645,640 | 7/1953 | Charpentier | 260/243 |
| 3,177,211 | 4/1965 | Zenitz | 544/42 |
| 3,313,810 | 4/1967 | Nakanshi | 544/42 |
| 3,637,679 | 1/1972 | Lovell | 260/243 |
| 3,966,930 | 6/1976 | Buus | 544/42 |
| 4,049,419 | 9/1977 | D'Amico | 548/173 |
| 4,548,934 | 10/1985 | Fengler | 544/51 |

FOREIGN PATENT DOCUMENTS 239427  4/1987  Czechoslovakia .

OTHER PUBLICATIONS

Chemical Abstracts 51.12101 (b), (c) 1957 (Fujii).

*Primary Examiner*—Robert Gerstl
*Attorney, Agent, or Firm*—The Firm of Gordon W. Hueschen

[57] ABSTRACT

A compound of formula (I):

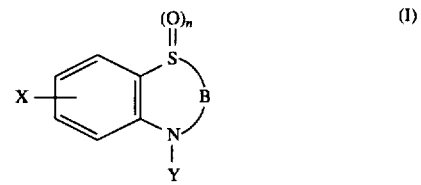

in which X, n, B and Y are as defined in the description. useful as cytokine inhibitors.

5 Claims, 1 Drawing Sheet

HETEROCYCLIC COMPOUNDS

The present application is a division of our prior-filed application Ser. No. 08/066,524, filed May 24, 1993, now abandoned.

The present invention relates to new heterocyclic compounds, a process for the preparation thereof and pharmaceutical compositions containing them. Some heterocyclic compounds similar to those of the present invention have been described in patents U.S. Pat. No. 2,519,886 and U.S. Pat. No. 2,645,640 for their antidyspnoeic, anti-asthmatic, ganglioplegic, spasmolytic or analgesic properties.

Apart from being new, the compounds of the present invention exhibit an inhibitory activity with respect to cytokines, including tumour necrosis factor (TNF), and therefore have a novel application in disorders capable of inducing septic shock, inflammatory disorders, rejection of transplanted organs, pain, hypertension, . . . .

Figure 1:
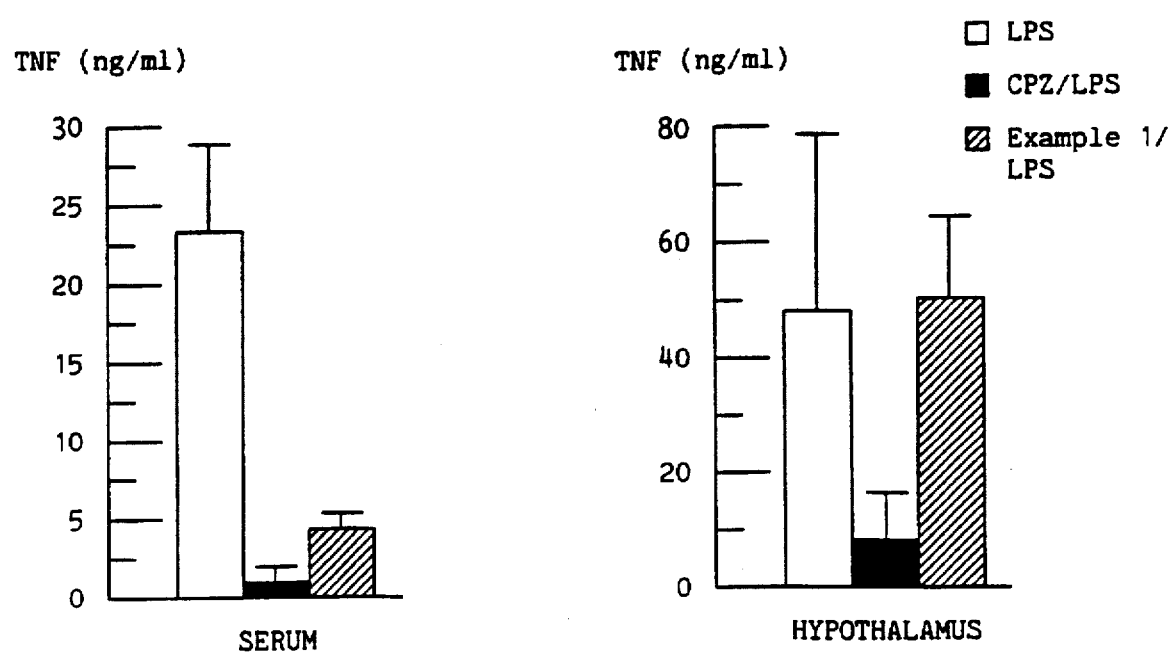
FIG. 1 is a drawing showing the peripheral effect of the compounds of the invention as compared with chlorpromazine, which also reduces the amount of TNF in the serum.

The present invention relates more especially to the compounds of the general formula (I):

(I)

in which:
X represents halogen selected from fluorine, chlorine, bromine and iodine,
n represents 0, 1 or 2,
B represents one of the groupings $B_1$, $B_2$ and $B_3$ of the formulae:

($B_1$)   ($B_2$)   ($B_3$)

in which:
each of $R_1$ and $R_2$, independently of the other, represents hydrogen, an alkyl grouping that is optionally substituted and contains from 1 to 5 carbon atoms in a straight or branched chain, an optionally substituted aryl grouping, an optionally substituted arylalkyl grouping or an optionally substituted heteroaryl grouping,
or $R_1$ and $R_2$ together form an aromatic ring that contains 6 carbon atoms and is optionally substituted by a grouping X' representing halogen selected from fluorine, chlorine, bromine and iodine,
$R_3$ represents hydrogen, an optionally substituted aryl grouping, an optionally substituted arylalkyl grouping or an optionally substituted heteroaryl grouping, A represents either:
* the radical $+SO_2 \frac{}{x} Alk-Z$ in which x represents 0 or 1, Alk represents a saturated bivalent hydrocarbon radical containing from 3 to 6 carbon atoms in a straight or branched chain, and Z represents a radical selected from the group consisting of:
a) nitrile, carboxy or alkoxycarbonyl,
b) the radical in which:
$T_1$, $T_2$ and $T_3$, which may be identical or different, are selected from linear or branched alkyl radicals containing from 1 to 5 carbon atoms, optionally substituted aryl radicals and optionally substituted arylalkyl radicals,
Q represents a halogen atom selected from chlorine, bromine and iodine, or a residue of a weak acid, such as an acetate, fumarate, triflate, . . .
c) the radical in which each of m and p, independently of the other, represents 1 or 2, z represents aninteger from 0 to (m+2) inclusive and R represents an alkyl radical containing from 1 to 5 carbon atoms in a straight or branched chain, aryl or arylalkyl, each of which is optionally substituted,
d) the radical in which $R_4$ represents hydrogen, carboxy, alkoxycarbonyl, or an optionally substituted aminocarbonyl radical,
e) the radical in which each of W and W', independently of the other, represents $H_2$, O or S, t represents 0 or 1, r represents 1 or 2, q represents an integer from 0 to (r+2) inclusive and R is as defined above, f) the radical

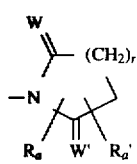

in which W, W' and r are as defined above and each of $R_a$ and $R'_a$, independently of the other, represents hydrogen, alkyl containing from 1 to 5 carbon atoms in a straight or branched chain, optionally substituted aryl or optionally substituted arylalkyl, g) the radical

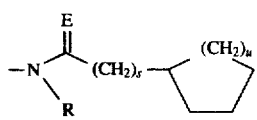

in which E represents O, S or the grouping N-H, each of s and u, independently of the other, represents 1 or 2 and R is as defined above,

* or the radical

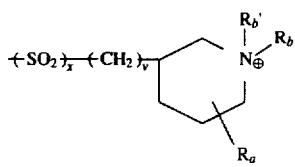

in which v represents an integer from 1 to 4 inclusive, $R_a$ and x are as defined above and each of Rb and R'b, independently, of the other, represents an alkyl radical containing from 1 to 5 carbon atoms in a straight or branched chain, an optionaly substituted aryl radical or an optionaly substituted arylalkyl radical,

* or, when B represents the radical $B_3$ defined above, the radical

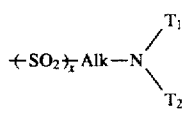

in which x, Alk, $T_1$ and $T_2$ are as defined above,
* or the radical

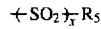

in which x is as defined above and $R_5$ represents a hydrocarbon radical containing from 5 to 20 carbon atoms in a straight or branched chain and including at least one unsaturation in the form of a double bond,
and Y' forms a bond with Y, and Y, when B represents the radical $B_1$ or $B_2$, represents the grouping A as defined above,
with the following restrictions:
when B represents the grouping $B_2$, when A simultaneously represents the radical $-(SO_2)_x$-Alk-Z and when X simultaneously is different from 0, Z may not represent a nitrile radical or a carboxy radical or an alkoxycarbonyl radical, when B represents the radical $B_1$ in which $R_1$ and $R_2$ together form an aromatic ring having 6 carbon atoms and when A simultaneously represents the radical

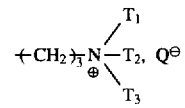

$Q^\ominus$ may represent only the anion $Br^\ominus$, it being understood that, else otherwise specified, "aryl radical" represents a radical chosen among phenyl and naphtyl, "arylalkyl radical" represents a radical chosen among phenyl and naphtyl bound to an alkyl radical containing from 1 to 4 atoms, and "heteroaryl radical" represents a radical chosen among pyridyl, pyrrolyl, pyrazinyl, pyridazinyl, pyrimidazinyl, quinolyl and indolyl, it being also understood that, else otherwise specified, the expression "optionally substituted" means that the alkyl, aryl, arylalkyl or heteroaryl groupings may be substituted by one or more species chosen among halogen atoms, hydroxy, nitro, cyano, alkyl, alkoxy, acyl, haloalkyl, amino, alkylamino and dialkylamino groupings. and their possible stereoisomers, epimers, N-oxides and addition salts with a pharmaceutically acceptable acid or base.

Of the pharmaceutically acceptable acids that may be used to form an addition salt with the compounds of the invention, there may be mentioned by way of non-limiting examples: hydrochloric, phosphoric, sulfuric, tartaric, citric, maleic, fumaric, alkylsulfonic and camphoric acid. Of the pharmaceutically acceptable bases that may be used to form an addition salt with the compounds of the invention, there may be mentioned by way of non-limiting examples: sodium and potassium hydroxide, diethylamine, triethylamine, ethanolamine, diethanolamine, arginine and lysine.

The present invention relates also to a process for the preparation of the compounds of the formula (I), characterised in that the starting material is:

a) —either the compound of the formula (II):

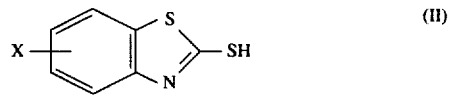

in which X is as defined for formula (I),
which is treated with sulfuryl chloride at ambient temperature to yield the compound of the formula (III):

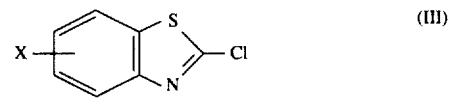

in which X is as defined above,
then with an amine of the formula $H_2N$-$R_3$, in which $R_3$ is as defined above, to give the compound of the formula (IV):

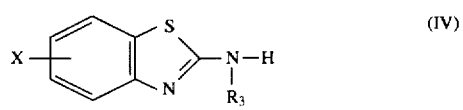

in which X and $R_3$ are as defined above, b) —or the compound of the formula (V):

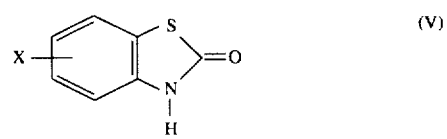

in which X is as defined above, c) —or the compound of the formula (VI):

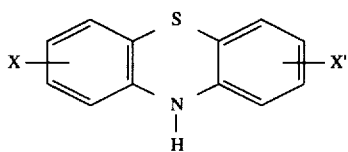
(VI)

in which X and X' are as defined above,
the compounds of formulae (IV), (V) and (VI) forming all of the compounds of the formula (VII):

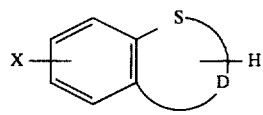
(VII)

in which X is as defined above and D represents one of the groupings $D_1$, $D_2$ and $D_3$ of the formulae:

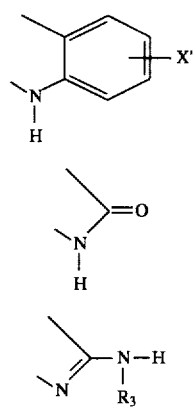

($D_1$)

($D_2$)

($D_3$)

in which X' and $R_3$ are as defined above,
which are optionally oxidised:

- to form the S-monoxide by means of a suitable reagent, for example nitric acid, which is then neutralised with an alkaline solution, for example of sodium hydroxide, or
- to form the S-dioxide, after eventual protection of the nitrogen atom, for example using acetic anhydride, with a suitable oxidising agent, such as hydrogen peroxide in acetic acid, in such a manner as to obtain the compounds of the formula (VIII):

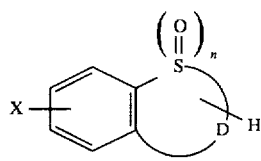
(VIII)

in which X, n and D are as defined above, which are subjected:

a) either to alkylation, for example, using sodium amide, in a solvent, such as xylene, under reflux, with the compound of the formula (IX):

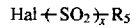  (IX)

in which x and $R_5$ are as defined above and Hal represents a halogen atom, to obtain the compounds of the formula (X):

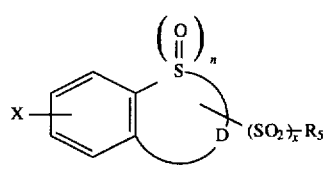
(X)

in which X, n, D, x and $R_5$ are as defined above, b) or to alkylation, for example, using sodium amide in a suitable solvent, such as xylene or dioxane, with a compound of the formula (XI):

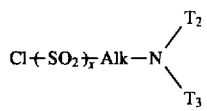
(XI)

in which x, Alk, $T_2$ and $T_3$ are as defined above, to give the compound of the formula (XII):

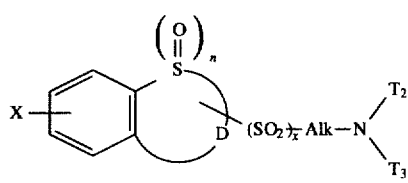
(XII)

in which X, n, D, x, Alk, $T_2$ and $T_3$ are as defined above, which is optionally converted by the compound of the formula (XIII):

  (XIII)

in which $T_1$ and Q are as defined above,
into a quaternary ammonium salt of the formula (XIV):

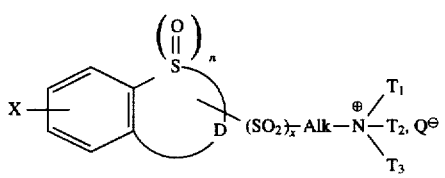
(XIV)

in which X, n, D, x, Alk, $T_1$, $T_2$, $T_3$ and Q are as defined above, c) or to alkylation, for example, using tetrabutyl-ammonium hydrogenosulfate, in a ketone/base mixture, for example methyl isobutyl ketone/sodium hydroxide, with the compound of the formula (XV):

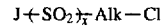  (XV)

in which x and Alk are as defined above and J represents a chlorine or bromine atom, to yield a compound of the formula (XVI):

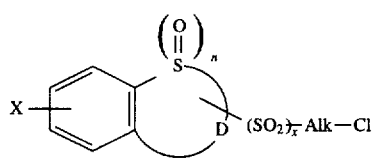
(XVI)

in which X, n, D, x and Alk are as defined above, which is treated with:

α) tetramethylammonium cyanide in the presence of an alcohol, for example isopropanol, to yield the compound of the formula (XVII):

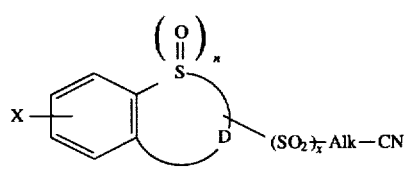
(XVII)

in which X, n, D, x and Alk are as defined above, which, by optional hydrolysis, gives the compound of the formula (XVIII):

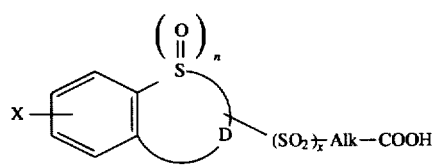
(XVIII)

in which X, n, D, x and Alk are as defined above, which may be converted into corresponding esters or amides in accordance with conventional methods, β) one of the following compounds:

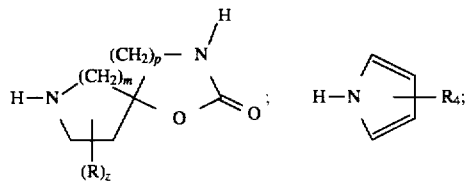

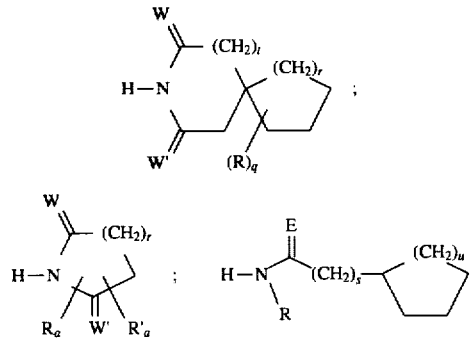

in which m, p, q, r, s, t, u, z, R, $R_a$, $R'_a$, $R_4$, E, W and W' are as defined above, in the presence of an alkali metal salt, an alkali metal base and a crown ether, to yield, respectively, the compounds of the following formulae (XIXa) to (XIXe):

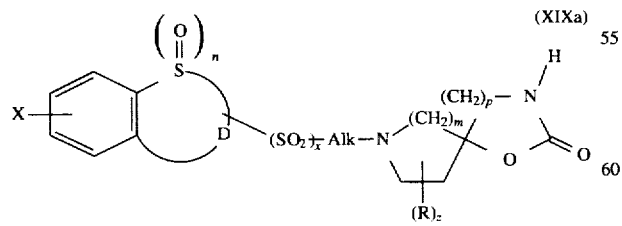
(XIXa)

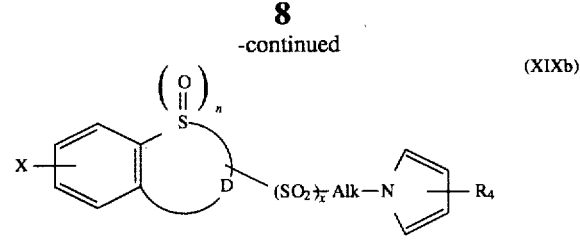
(XIXb)

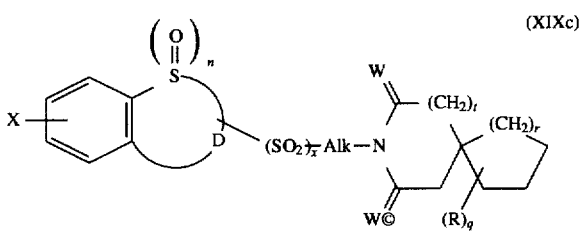
(XIXc)

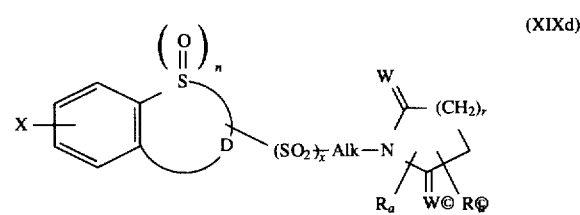
(XIXd)

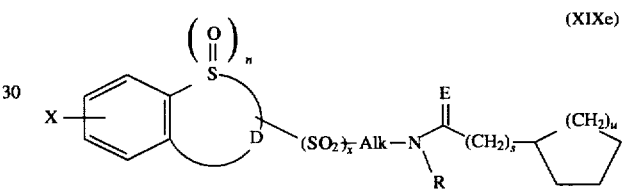
(XIXe)

in which m, n, p, q, r, s, t, u, x, z, Alk, D, E, R, $R_a$, $R'_a$, $R_4$, W, W' and X are as defined above, d) or to alkylation, for example, using tetrabutyl-ammonium sulfate, in a ketone/base mixture, for example methyl isobutyl ketone/sodium hydroxide, with the compound of the formula (XX):

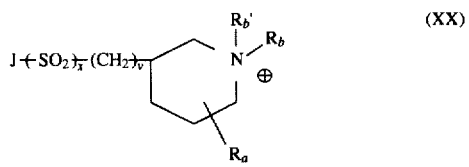
(XX)

in which J, $R_a$, $R_b$, $R'_b$, x and v are as defined above, to yield the compound of the formula (XXI):

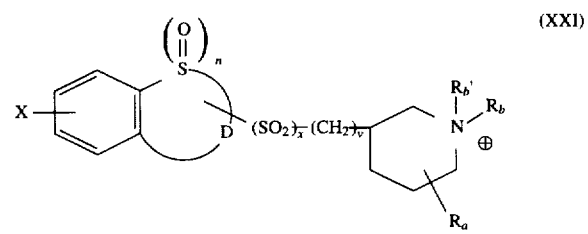
(XXI)

in which X, n, D, x, v, $R_a$, $R_b$ and $R'_b$ are as defined above, it being possible to subject the compounds of the formulae (x), (xzz), (xvzz), (xzxa)to (xzxe)or (xx)

When D represents the grouping

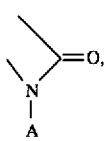

in which A is as defined above, to the action of a base in an alcohol solvent, for example in potassium hydroxide in ethanol, then to acidification, for example using acetic acid, to yield the compound of the formula (XXII):

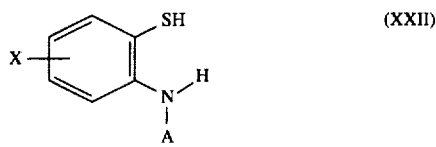

in which X and A are as defined above, which is treated in an alkaline medium for example potassium hydroxide in ethanol, with a compound of the formula (XXIII):

in which each of $R'_1$ and $R'_2$, independently of the other, represents a hydrogen atom, an optionally substituted alkyl grouping containing from 1 to 5 carbon atoms in a straight or branched chain, an optionally substituted aryl grouping or an optionally substituted heteroaryl grouping, to yield the compound of the formula (XXIV):

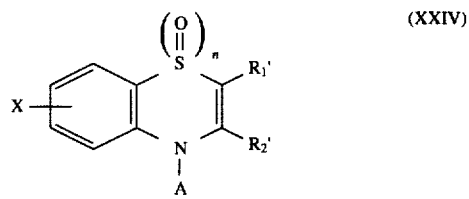

in which X, A, n, $R'_1$ and $R'_2$ are as defined above, all of the compounds of formulae (X), (XII), (XIV), (XVII), (XVIII), (XIXa) to (XIXe), (XX), (XXI) and (XXIV) forming all of the compounds of the formula (I), which are purified, where appropriate, in accordance with a conventional purification technique and the stereoisomers of which are, if desired, separated by a conventional separation technique, and which are converted, if necessary, into their addition salts with a pharmaceutically acceptable acid or base, which compounds, when n=0, may be oxidised to form the corresponding S-oxide or S-dioxide.

The compounds of the formula (I) have new pharmacological properties. When administered to mice, they inhibit the production of tumour necrosis factor (TNF) which is involved in a large number of pathological conditions ranging from inflammation to septic shock.

TNF is a cytokine that is secreted after the activation of macrophages, monocytes or other immunocompetent cells and which, once released into the circulation and the tissues, binds to specific receptors. With interleukin-1 (IL-1), it o plays a decisive role in the occurrence of inflammatory and metabolic effects. The biological and/or pathological effects are manifold: fever, capillary leakage, intravascular coagulation, inflammation, loss of proteins, cachexia . . .

The following Examples illustrate the invention without limiting it in any way. The starting materials are known or are prepared on the basis of known procedures.

Preparation A: Preparation of 2-chloro-10-(3-dimethylaminopropyl)phenothiazine 3.56 g (10 mmol) of 2-chloro-10-(3-dimethylaminopropyl) phenothiazine hydrochloride are suspended in 15 ml of a 1N sodium hydroxide solution. The amine freed is extracted with diethyl ether. The organic phase is decanted and dried over sodium sulfate and then evaporated to dryness to yield 3.13 g of an oil corresponding to the expected product.
Yield: 98%

Preparation B: Nitrate of 2-chloro-10-(3-dimethylaminopropyl)phenothiazine-5-oxide A solution of 3.56 g (10 mmol) of 2-chloro-10-(3-dimethylaminopropyl)phenothiazine hydrochloride in 50 ml of water is added dropwise to 5.5 ml of a 11N nitric acid solution. The mixture is stirred at ambient temperature for 30 minutes. The pH is then adjusted to from 3 to 4 by adding a 1N sodium hydroxide solution. After stirring for 15 hours at 0° C., the expected product crystallises. After filtering and drying in a vacuum over phosphoric acid, 3.7 g of the expected product are obtained.
Yield: 93%
Melting point: 102°–104° C.

Preparation C:
2-chloro-10-(3-dimethylaminopropyl)phenothiazine-5-dioxide

Stage a/ 2-chloro-10-acetylphenothiazine-5-dioxide 4.2 g (15 mmol) of 2-chloro-10-acetylphenothiazine are dissolved in 30 ml of glacial acetic acid. 3.25 ml of a hydrogen peroxide solution (20% in water) are added. The mixture is heated at 90° C. for 4 hours 30 minutes. After returning to ambient temperature, the addition of water causes the expected product to precipitate. After filtering, washing with water and drying under a vacuum over phosphoric acid, 4 g of sulfone are obtained.
Yield: 87%
Melting point: 195°–197° C.

Stage b/ 2-chlorophenothiazine-5-dioxide

The sulfone obtained in stage a/ is stirred in 100 ml of a 1:1 mixture of 1N sodium hydroxide and ethanol. After two hours' reaction under reflux, the ethanol is evaporated. The precipitate is filtered, washed with water and then dried in a vacuum over phosphoric acid.
Yield: 96%
Melting point: 271°–273° C.

Stage c/ 2-chloro-10-(3-dimethylaminopropyl)phenothiazine-5-dioxide 1.17 g (30 mmol) of sodium amide are added to 5.3 g (20 mmol) of the sulfone obtained previously in 200 ml of dioxane. The mixture is heated under reflux for 3 hours. 4.9 g (40 mmol) of 3-chloro-N,N-dimethylpropylamine in 20 ml of toluene are added to the previous solution. After heating under reflux for 20 hours, the solid formed is removed by filtration. 3 g of product are obtained after evaporating the solvent and recrystallising from ethanol.
Yield: 60%
Melting point: 105°–106° C.

Preparation D: 2-chloro-10-(3-chloropropyl)phenothiazine 40 ml of a sodium hydroxide solution (50% by weight) are added to a solution of 2.34 g (10 mmol) of 2-chlorophenothiazine, 4.73 g (30 mmol) of 1-bromo-3-chloropropane and 0.34 g (1 mmol) of tetrabutylammonium hydrogenosulfate in 40 ml of 4-methylpentan-2-one. The mixture is stirred at ambient temperature for 48 hours. After customary treatment of the organic phase, drying over sodium sulfate, evaporation of the solvent and purification by chromatography on silica gel, 2.17 g of pure product are obtained (eluant: petroleum ether).
Yield: 70%
Melting point: 51°–52° C.

Preparation E: 3-(3-dimethylammoniopropyl)-5-chlorobenzothiazolin-2-one chloride Compound prepared in accordance with the procedure described in preparation C, stage c), starting from 5-chlorobenzothiazol in-2-one.
Yield: 87%
Melting point: 206°–208° C.

Example 1: N-[3-(2-chlorophenothiazin-10-yl)propyl]trimethylammonium bromide 150 mmol of methyl bromide (2M solution in diethyl ether) are added at 0° C. under an argon atmosphere to 3.2 g (10 mmol) of the oil obtained in preparation A. After stirring for from 8 to 12 hours at ambient temperature, the compound formed is separated by filtration, washed with diethyl ether and dried under a vacuum over phosphoric acid. 2.7 g of the expected product are obtained.
Yield: 65%
Melting point: 137°–140° C.

Example 2: N-[3-(2-chloro-5-oxo-phenothiazin-10-yl)propyl]trimethylammonium bromide The nitrate obtained in Example B is treated in a manner analogous to that described in preparation A. The free amine thus obtained is methylated in accordance with the method described in Example 1.
Yield: 95%
Melting point: 240°–243° C.

Example 3: N-[3-(2-chloro-5-dioxo-phenothiazin-10-yl)propyl]trimethylammonium bromide This compound is obtained in accordance with the procedure described in Example 1 using the sulfone of preparation C as starting material.
Yield: 73%
Melting point: 183°–184° C.

Example 4: N-[3-(2-chlorophenothiazin-10-yl)propyl]dimethylethylammonium bromide Synthesis identical with that described in Example 1, the alkylating agent this time being ethyl bromide.
Yield: 88%
Melting point: 176°–177° C.

Example 5: N-[3-(2-chlorophenothiazin-10-yl)propyl]dimethylpropylammonium bromide Same comment as for Example 4, the alkylation here being carried out with propyl bromide.
Yield: 66%
Melting point: 213°–215° C.

Example 6: .N-[3-(2-chlorophenothiazin-10-yl)propyl]dimethylisopropylammonium bromide Synthesis identical with that of Example. 5 using isopropyl bromide.
Yield: 61%
Melting point: 153°–154° C.

Example 7: N-[3-(2-chlorophenothiazin-10-yl)propyl]butyldimethylammonium bromide Same comment as for Example 4, the alkylating agent in this case being n-butyl bromide.
Yield: 68%
Melting point: 191° C.

Example 8: N-[3-(2-chloro-5-oxo-phenothiazin-10-yl)propyl]butyldimethylammonium bromide Synthesis analogous to that described in Example 2, the alkylating agent in this case being n-butyl bromide.
Yield: 81%
Melting point: 260°–264° C.

Example 9: N-[3-(2-chloro-5-dioxo-phenothiazin-10-yl)propyl]butyldimethylammonium bromide A solution of 1.75 g (5 mmol) of the sulfone obtained in preparation C in 20 ml of 1-bromobutane is heated under reflux for 8 hours and then stirred at ambient temperature for 12 hours. The precipitate obtained is filtered and then washed with a large amount of diethyl ether. After purification by recrystallisation from a methanol/ethanol mixture, 1.58 g of the expected product is obtained.
Yield: 65%
Melting point: 270°–274° C.

Example 10: N-[3-(2-chlorophenothiazin-10-yl)propyl]benzyldimethylammonium bromide 3.2 g (10 mmol) of the compound of preparation A are dissolved in 35 ml of tetrahydrofuran, and then 3.18 g (20 mmol) of benzyl bromide dissolved in tetrahydrofuran are added. The reaction mixture is heated under reflux for 15 hours. The precipitate formed, which is separated by filtration, washed with diethyl ether and then dried under a vacuum over phosphoric acid, yields 2.84 g of the expected product.
Yield: 58%
Melting point: 140°–142° C.

13

Example 11: Methyl 1-[3-(2-chlorophenothiazin-10-yl)-1-propyl]pyrrole-2-carboxylate 3.17 g (25 mmol) of methyl pyrrole-2-carboxylate, 2.07 g (15 mmol) of potassium carbonate, 27.5 ml of potassium hydroxide and 0.66 g (2.5 mmol) of 18-crown-6 ether, in solution in 120 ml of toluene, are introduced in succession under an argon atmosphere. Stirring for 2 hours at ambient temperature causes the pyrrole anion to precipitate. 7.75 g (25 mmol) of the compound obtained in preparation D in 25 ml of toluene are added dropwise. The mixture is then heated under reflux for 6 hours. After hydrolysing with a saturated solution of potassium chloride, extracting with diethyl ether and washing the combined organic phases with water, the organic phases are dried over sodium sulfate and the solvent is evaporated. After purification by chromatography on silica gel, 5.98 g of the expected product are obtained (eluant: dichloromethane/cyclohexane).
Yield: 60%
Melting point: 90°–92° C.

Example 12: 1-[3-(2-chlorophenothiazin-10-yl)-1-propyl]pyrrole-2-carboxylic acid 3.99 g (10 mmol) of the compound obtained in Example 11 are dissolved in 15 ml of ethanol and 7.5 ml of dimethyl sulfoxide. 0.8 g (20 mmol) of sodium hydroxide (in 1N solution) is added and the mixture is heated under reflux for 7 hours, with stirring. After acidification with a 1N hydrochloric acid solution and customary treatment of the organic phases, 3.62 g of the expected product are obtained.
Yield: 94%
Melting point: 162°–163° C.

Example 13: 8-[3-(2-chlorophenothiazin-10-yl)-1-propyl]-2-oxo-3,8-diaza-1-oxa-spiro[4.5] decan-2-one Reaction identical with that described in Example 11, by condensing 3,8-diaza-1-oxa-spirodecan-2-one (compound described in U.S. Pat. No. 3,594,386). 6.01 g of product are obtained after recrystallisation from ethyl acetate.
Yield: 56%
Melting point: 142°–143° C.

Example 14: 2-chloro-10-[1-(4-cyanopropyl)]phenothiazine 1.7 g (12 mmol) of tetraethylammonium cyanide in 12 ml of isopropanol are added to 2.48 g (8 mmol) of the compound of Example D in solution in 25 ml of isopropanol. The mixture is heated under reflux for 72 hours. After evaporation of the isopropanol, tetraethylammonium chloride is precipitated by diethyl ether and removed by filtration. Purification by chromatography on silica gel (eluant: cyclohexane/ethyl acetate) yields 2.10 g of the expected product.
Yield: 87%
Melting point: 75°–77° C.

Example 15: 4-(2-chlorophenothiazin-10-yl)butanoic acid 2.10 g (7 mmol) of the product of Example 14 are dissolved in 20 ml of ethanol. 1.57 g (28 mmol) of potassium hydroxide in solution in 10 ml of water are added and the mixture is heated under reflux for 12 hours and then left to stand overnight at ambient temperature. The medium is then acidified with a 1N hydrochloric acid solution. Treatment of the organic phase with dichloromethane then acetone yields 1.17 g of acid.
Yield: 52%
Melting point: 142°–144° C.

Example 16: N-[3-(5-chlorobenzothiazolin-2-on-3-yl)propyl]trimethylammonium iodide Compound prepared starting from the product obtained in Example E in accordance with the procedure described in Example 1.
Yield: 56%
Melting point: 202°–204° C.

Example 17: Methyl 1-[3-(5-chloro-2-oxo-benzothiazolin-3-yl)-1-propyl]pyrrole-2-carboxylate Compound prepared in accordance with the procedures described in preparation D and then in Example 11 from 5-chlorobenzothiazolin-2-one.
Yield: 40%
Melting point: 90°–91° C.

Example 18: 1-[3-(5-chloro-2-oxo-benzothiazolin-3-yl)-1-propyl]pyrrole-2-carboxylic acid Compound prepared in accordance with the procedure described in Example 12 from the compound obtained in the previous example.
Yield: 57%
Melting point: 162°–166° C.

Example 19: 5-chloro-3-[3-(8,8-dimethyl-1,3-dioxo-2-azaspiro [4.5] decan-2-yl)propyl]benzothiazolin-2-one Stage a/ 3-(3-azidopropyl)-5-chlorobenzothiazolin-2-one
2.62 g (10 mmol) of 3-(3-chloropropyl)-5-chlorobenzothiazolin-2-one, 0.98 g (15 mmol) of sodium azide and a catalytic amount of potassium iodide are dissolved in 40 ml of dimethyl sulfoxide. The solution is heated at 55° C. for 25 hours, with stirring. Customary treatment of the organic phase yields the expected product.
Yield: 100%

Stage b/ 3-(3-aminopropyl)-5-chlorobenzothiazolin-2-one
0.46 g (12 mmol) of lithium aluminium hydride are suspended in 12 ml of anhydrous tetrahydrofuran under argon at 0° C. 2.15 g (8 mmol) of the compound obtained in stage a/ are added. The mixture is hydrolysed and the organic phase is washed with a dichloromethane/methanol mixture to give the expected product.
Yield: 71%

Stage c/ 5-chloro-3-[3-(8,8-dimethyl-1,3-dioxo-2-azaspiro-[4.5]decan-2-yl)propyl]benzothiazolin-2-one
An equimolar mixture of the compound obtained in stage b/ and 8,8-dimethyl-2-oxaspiro[4.5]decane-1,3-dione in toluene is heated under reflux for 4 days in the presence of a molecular sieve. After removing the molecular sieve and evaporating the solvent, the expected product is obtained.
Yield: 35%
Melting point: 159°–160° C.

Example 20: 2-[3-(2-chlorophenothiazin-10-yl)-1-propyl]-7,7,9,9-tetramethyl-2-azaspiro[4.5]decane-1,3-dione Compound prepared in a manner identical with that of the compound of Example 19.

Example 21:
2-[3-(2-chlorophenothiazin-10-yl)-1-propyl]-7,9-dimethyl-2-azaspiro[4.5]decane-1,3-dione Compound prepared in a manner identical with that of the compound of Example 19.

Example 22: N-[3-(2-chlorophenothiazin-10-yl)sulfonylpropyl]trimethylammonium bromide Stage a/ 2-chloro-10-[(3-chloropropyl)sulfonyl]phenothiazine A mixture of 11.68 g (50 mmol) of 2-chlorophenothiazine and 2.34 g (60 mmol) of sodium amide in 100 ml of xylene is heated under reflux for from 1 to 2 hours. 50 ml of 3-chloropropylsulfonyl chloride in 25 ml of xylene are added and then the mixture is heated under reflux again for one night. After cooling of the reaction medium and filtering the solid residue, the filtrate is evaporated to dryness. After distillation under reduced pressure, an oil corresponding to the title product is obtained.

Stage b/ 2-chloro-10-[(3-dimethylaminopropyl)sulfonyl]phenothiazine

The chloro compound obtained in stage a/ (2 g) is dissolved in 45 ml of dimethylamine in an autoclave at ambient temperature. After 24 hours' reaction, the amine is evaporated at ambient temperature and the solid residue is taken up in ether.

The ammonium salts are precipitated in the form of the hydrochloride by adding an ethereal solution of hydrochloric acid. After filtration, the solid is taken up in a 1N sodium hydroxide solution and extracted with ether. Drying and evaporation of the organic phase yields 1.75 g of the expected product.

Stage c/ N-[3-(2-chlorophenothiazin-10-yl)sulfonylpropyl]trimethylammonium bromide The quaternary ammonium is formed starting from the amine obtained in stage b/ using the reaction conditions indicated in Example 1.
Yield: 40%
Melting point: 216°–217° C.

Example 23:
N-[3-(6-chloro-3-phenyl-4H-1,4-benzothiazin-4-yl)propyl]trimethylammonium bromide Stage a/ 4-chloro-2-(3,3-dimethylaminopropyl)aminothiophenol 9.4 g (167.7 mmol) of potassium hydroxide are added to 11.35 g of the compound obtained in preparation E (41.9 mmol) in 50 ml of ethanol. The mixture is heated under reflux for 2 hours and then the solvent is evaporated.

The oily residue is taken up in 100 ml of water, washed with toluene and then acidified with 10% acetic acid. The oil thencrystallises to give 6.2 g of the expected product after filtration.
Yield: 60%
Stage b/ 4-(3,3-dimethylaminopropyl)-3-phenyl-6-chlorobenzothiazine 7.34 g (30 mmol) of the compound obtained in stage a/ are added under argon to a solution of 1.68 g of potassium hydroxide (30 mmol) in 45 ml of ethanol. 6.86 g (34.5 mmol) of bromoacetophenone dissolved in 80 ml of ethanol are then added dropwise. The mixture is heated under reflux for 20 hours.

After evaporating the solvent, the medium is taken up in 10% acetic acid, washed with ether and rendered alkaline with a concentrated sodium hydroxide solution. Extraction of this basic aqueous phase with ether yields, after drying over sodium sulfate, evaporation and purification by chromatography on silica gel, 5.6 g of 1-{[4-chloro-2-(3,3-dimethylpropyl)amino]phenylthio}acetophenone which are solubilized in toluene, with boron trifluoride/ethylic ether complex, and heated under reflux for 2 hours 20 minutes to yield 1.8 g of the expected bicyclic compound in the form of an oil.
Yield: 34%
Stage c/ N-[3-(6-chloro-3-phenyl-4H-1,4-benzothiazin-4-yl) propyl]trimethylammonium bromide 0.53 g of the compound obtained in stage b/ is treated in a manner analogous to that described in Example 1 to yield 0.48 g of quaternary ammonium.
Yield: 72%
Melting point: 225°–226° C.

Example 24: 2-(3-dimethylammoniopropylamino)-5-chlorobenzothiazolium dichloride Stage a/ 2,5-dichlorobenzothiazole 9.15 g of 5-chloro-2-mercaptobenzothiazole are reacted in 50 ml of sulfuryl chloride at ambient temperature for 1 hour 30 minutes. After hydrolysis, extraction of the aqueous phase with dichloromethane and customary treatment of the organic phase, 8.3 g of the expected product are obtained.
Yield: 90%
Melting point: 63°–64° C.
Stage b/ 2-[(3-dimethylaminopropyl)amino]-5-chlorobenzothiazole Compound obtained in accordance with the procedure described in Example 11 using 3,5-dichlorobenzothiazole and N,N-dimethylaminopropylamine.
Yield: 70%
Stage c/ 2-(3-dimethylammoniopropylamino)-5-chlorobenzothiazoliumdichloride The compound obtained in stage b/ is taken up in ethanol. The hydrochloride is formed by the addition of a saturated solution of hydrochloric acid in ethanol.
Yield: 90%
Melting point: 275°–276° C.

Example 25: N-(3-dimethylammonio-1-propyl)-N-(3-pyridiniomethyl)-2-amino-5-chlorobenzothiazolium trichloride Condensation of 0.6 g of 1,1-dimethyl-3-[(pyrid-3-yl)methylamino]propylamine (obtained by hydrogenation of the reaction product of 2-formylpyridine with 3-(N,N-dimethylamino)propylamine) with 0.7 g of 2,5-dichlorobenzothiazole yields the expected tertiary amine in accordance with the procedure described in Example 11. The hydrochloride is then formed by taking up the crude product in a solution of hydrochloric acid in ethanol. The addition of ether to the medium precipitates 0.45 g of tri-salt compound.
Yield: 34%
Melting point: 236°–238° C.

Example 26: 2-chloro-10-[(2E)-1-(3,7-dimethylocta-2,6-dienyl)]phenothiazine

Compound obtained in accordance with the procedure described in preparation C, stage c/, starting from 2-chlorophenothiazine and (2E)-1-chloro-3,7-dimethylocta-2,6-diene.
Yield: 20%

Example 27:
2-[3-(2-chlorophenothiazin-10-yl)propyl]-8-tert-butyl-2-azoniaspiro[4.5]decane chloride Compound prepared in a manner identical with that for the compound of Example 19.
Melting point: 227°–228° C.

Example 28:
2-[3-(2-chlorophenothiazin-10-yl)propyl]-8,8-dimethyl-2-azoniaspiro[4.5]decane chloride Compound prepared in a manner identical with that for the compound of Example 19.
Melting point: 100°–105° C.

Example 29: [N-(5-chlorobenzothiazol-2-yl)ammonio]propyltrimethylammonium dibromide The quaternary ammonium salt is prepared using the compound of Example 24 in a mamer identical with that for the compound of Example 1. The salt is then taken up in ethanol and treated with a saturated solution of bromhydric acid in ethanol. The so formed hydrobromide is isolated by filtration.

Example 30: bis-(5-chlorobenzothiazol-2-yl)-3-dimethylaminopropyl)ammonium chloride Compound prepared in a mamer identical with that for the compound of Example 11 using 2 equivalents of 3,5-dichlorobenzothiazole and 1 equivalent of N,N-dimethylaminopropylamine. The corresponding hydrochloride is then prepared in a manner identical with that for the compound of Example 24, stage c/
Yield: 10%
Melting point>250° C.

PHARMACOLOGICAL STUDY

Example 31: Inhibition of the production of TNF

The test is carried out on mice. Thirty minutes after the intraperitoneal or oral administration of the molecule to be tested, the mice are treated intraperitoneally with 2.5 µg of LPS from *Escherichia coli*. The amount of TNF in the serum is measured after 1 hour by a biological method.

TABLE I

| Inhibition of the production of TNF (compared with control group which has received only LPS) | | |
|---|---|---|
| | % inhibition after admin. (dose) | |
| Compound | i.p. | oral |
| Example 1 | 75% (5 mg/kg) | 68% (50 mg/kg) |
| Example 2 | 50% (5 mg/kg) | 60% (50 mg/kg) |
| Example 3 | 69% (5 mg/kg) | — |
| Example 6 | 5— | 38% (50 mg/kg) |
| Example 7 | 95% (5 mg/kg) | 72% (50 mg/kg) |
| Example 8 | 71% (5 mg/kg) | 73% (50 mg/kg) |
| Example 9 | 75% (5 mg/kg) | — |
| Example 10 | 27% (5 mg/kg) | — |
| Example 15 | — | 55% (50 mg/kg) |

TABLE I-continued

| Inhibition of the production of TNF (compared with control group which has received only LPS) | | |
|---|---|---|
| | % inhibition after admin. (dose) | |
| Compound | i.p. | oral |
| Example 26 | — | 55% (50 mg/kg) |
| Example 27 | — | 26% (50 mg/kg) |
| Chlorpromazine | 100% (4 mg/kg) | — |

The compounds described here markedly reduce the amount of TNF in the serum and in some cases increase to a very pronounced extent the survival of mice to which endotoxin (or lipopolysaccharide (LPS)) has been administered intraperitoneally beforehand.

Example 32: Protective effect of the compounds in respect of LPS shock

The test is carried out on mice. The compound to be tested is administered intraperitoneally or orally. In the first protocol (i.p.), the compound is administered 30 minutes before the injection of 1 µg of LPS into mice. The mortality is determined 72 hours later.

TABLE II

| % Survival of mice after administration of LPS | |
|---|---|
| Compound | % survival 72 h after i.p. administration |
| Example 1 | 80% (5 mg/kg) |
| Example 7 | 40% (5 mg/kg) |
| Example 10 | 60% (5 mg/kg) |
| Chlorpromazine | 36% (1 mg/kg) |
| | 77% (4 mg/kg) |

Example 33: Peripheral effect of the compounds

In comparison with chlorpromazine, the compounds of the invention have only a peripheral effect. For example, the compound of Example 1 administered i.p. (8 mg/kg) to rats which then receive an intracerebroventricular injection of LPS, reduces the amount of TNF in the serum, as does chlorpromazine, but not the amount in the brain, as is observed in rats treated with chlorpromazine (FIG. I).

Example 34: Locomotive activity in mice

This test consists in determining the spontaneous motor activity of mice placed in an enclosure that constitutes a new environment and is equipped with a system of infra-red rays, the interruption of which when the animal passes through serves as a measurement criterion ("Activity monitor" Digiscan-Omnitech Electronics, Sufraco France).

The molecules are administered intraperitoneally 30 minutes before the test at doses of 1, 2, 2.5, 4, 5 and 10 mg/kg. The locomotive activity (number of movements) is measured for 15 minutes.

Unlike chlorpromazine, the compounds are found to have little or no sedative action (see Table III).

TABLE III

| DOSE IP | Number of movements (as a % compared with a control group) | | | | | |
|---|---|---|---|---|---|---|
|  | 1 mg/kg | 2 mg/kg | 2,5 mg/kg | 4 mg/kg | 5 mg/kg | 10 mg/kg |
| Example 1 |  |  |  |  | −20% ns | −9% ns |
| Example 7 |  |  | −27% ns |  | −43%** | −63%** |
| Chlorpromazine | −20% ns | −58% |  | −64% |  |  | ns stands for p > 0.05
**stands for p < 0.01

The difference observed between chlorpromazine (very sedative at 2 mg/kg and above while the effective dose is 4 mg/kg) and the compounds studied is due to their limited passage through the blood/brain barrier as is demonstrated by the determination of corticosteronemia after the administration of IL-1.

Example 35: Measurement of corticosteronemia after administration of IL-1

Thirty minutes after the intraperitoneal administration of the molecule to be tested, the mice are treated with 1 μg of IL-1 injected intraperitoneally. Corticosteronemia is determined 2 hours later by a suitable technique.

Under the same conditions, the compound and then a saline solution are administered intraperitoneally to a control group. Under the influence of IL-1, corticosteronemia increases very substantially (control:+735%). The compounds claimed do not alter the basal amount of corticosterone to any appreciable extent.

After the administration of IL-1, the levels of corticosteronemia also are not different from that observed in the controls. On the other hand, chlorpromazine (which crosses the blood/brain barrier) reduces hypercorticosteronemia by the order of 86%.

TABLE IV

| Hypercorticosteronemia after administration of IL-1 (ng of corticosterone/ml of serum) | | |
|---|---|---|
| Compound (5 mg/kg) | Hyper-corticostéronémia after admin. IL-1 (ng/ml sérum) | Réduction in l'hyper-corticostéronémia compared with control |
| Example 1 | 389 | 11.8% |
| Example 2 | 417 | 5.4% |
| Example 7 | 389 | 11.8% |
| Example 8 | 356 | 19.3% |
| Example 10 | 440 | 0.2% |
| Chloropromazine (4 mg/kg) | 63 | 85.7% |
| Contrôle | 441 | — |

Example 36: Hypotensive effect

Unlike chlorpromazine, the compounds have no hypotensive effect whatsoever on rats.

No hypotension is observed when 20 mg/kg of the compounds of Examples 1, 2, 7 and 8 are administered intraperitoneally to rats. This is not the case with chlorpromazine which, at the same dose, brings about severe hypotension from the 15th minute onwards.

Example 37: Inhibition of phospholipase PLA$_2$ activity in pigs

In addition to their effect on TNF, the molecules also exhibit an inhibitory activity on phospholipase A$_2$ (PLA$_2$).

PLA$_2$ hydrolyses cell membrane phospholipids by freeing arachidonic acid (AA). Inhibition of that enzyme brings about a reduction in the amount of non-esterified free AA from which metabolites, such as leucotrienes and pro-inflammatory prostaglandins, are produced. The PLA$_2$ activity is measured by using as substrate $E.$ $coli$ membranes labelled with tritiated oleic acid. Procine pancreatic PLA$_2$ is incubated with the preparation for 30 minutes at 37° C. After centrifugation, the radioactivity of the supernatant is counted. The inhibitory activity of the compound (1 mM) is expressed in relation to the control.

TABLE VI

| Compound | % Inhibition at 1 mM |
|---|---|
| Example 1 | 72% |
| Example 7 | 97% |
| Example 10 | 98% |
| Chlorpromazine | 76% |
| Mepacrine | 67% |

We claim:

1. A compound selected from those of formula (I):

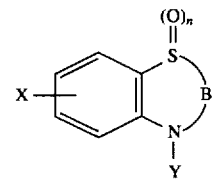

in which:

X represents halogen, n represents 0, 1, or 2,

B represents groups

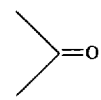

in which:

A represents either:

* the radical

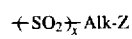

in which x represents 0 or 1, Alk represents a saturated bivalent hydrocarbon radical having from 3 to 6 carbon atoms inclusive in a straight or branched chain, and Z represents a radical selected from the group consisting of:

a) nitrile, carboxy or alkoxycarbonyl, b) the radical

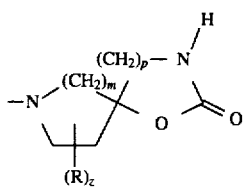

in which each of m and p, independently of the other, represents 1 or 2, z represents 0 to (m+2) inclusive and R represents alkyl having 1 to 5 carbon atoms inclusive in a straight or branched chain, aryl, or arylalkyl, each of which is optionally substituted, c) the radical

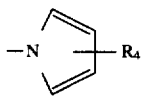

in which $R_4$ represents hydrogen, carboxy, alkoxycarbonyl, or optionally substituted aminocarbonyl, d) the radical

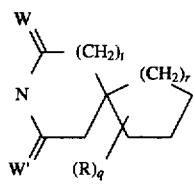

in which each of W and W', independently of the other, represents $H_2$, O or S, t represents 0 or 1, r represents 1 to 2, q represents 0 to (r+2) inclusive and R is as defined above, e) the radical

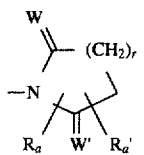

in which W, W' and r are as defined above and each of $R_a$ and $R'_a$, independently of the other, represents hydrogen, alkyl having 1 to 5 carbon atoms inclusive in a straight or branched chain, optionally substituted aryl, or optionally substituted arylalkyl, f) the radical

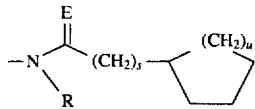

in which E represents O, S or the group N-H, each of s and u, independently of the other, represents 1 or 2 and R is as defined above,

* or the radical

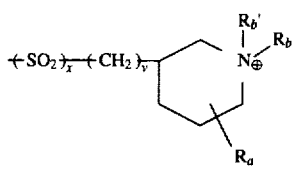

in which v represents 1 to 4 inclusive, $R_a$ and x are as defined above and each of $R_b$ and $R'_b$, independently of the other, represents alkyl having 1 to 5 carbon atoms inclusive in a straight or branched chain, optionally substituted aryl, or optionally substituted arylalkyl,

* or the radical

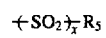

in which x is as defined above and $R_5$ represents a hydrocarbon radical having 5 to 20 carbon atoms inclusive in a straight or branched chain and including at least one unsaturation in the form of a double bond, and Y, represents the group A as defined above, with the following restrictions:

when A represents the radical $-(SO_2-)_x$Alk-Z and when x simultaneously is different from 0, Z must represent other than nitrile or carboxy or alkoxycarbonyl, it being understood that, unless otherwise specified, "aryl radical" represents a radical chosen from phenyl and naphtyl, "arylalkyl radical" represents a radical chosen from phenyl and naphthyl bound to an alkyl radical containing 1 to 4 carbon atoms inclusive and "heteroaryl radical" represents a radical chosen from pyridyl, pyrrolyl, pyrazinyl, pyridazinyl, pyrimidazinyl, quinolyl and indolyl, it being also understood that, unless otherwise specified, the expression "optionally substituted" means that the alkyl, aryl, arylalkyl or heteroaryl group may be substituted by one or more substituents chosen from halogen, hydroxy, nitro, cyano, alkyl, alkoxy, acyl, haloalkyl, amino, alkylamino and dialkylamino.

and their possible stereoisomers, epimers, N-oxides and addition salts with a pharmaceutically acceptable acid or base.

2. A method for treating a mammal afflicted with a condition requiring an inhibitor of cytokines, resulting from pain, the rejection of a transplanted organ, inflammatory disorders and disorders capable of inducing septic shock, comprising the step of administering to said living body an amount of a compound of claim 1 which is effective for alleviation of said condition.

3. A pharmaceutical composition useful in inhibiting cytokines which contains as active ingredient an effective amount of a compound according to claim 1, in combination with one or more pharmaceutically-acceptable, excipients or vehicles.

4. A compound of claim 1 which is methyl 1-pyrrole-2-carboxylate.

5. A compound of claim 1 which is 5-chloro-3-benzothiazolin-2-one.

* * * * *

UNITED STATES PATENT AND TRADEMARK OFFICE
CERTIFICATE OF CORRECTION

PATENT NO. : 5,550,143
DATED : Aug. 27, 1996       Page 1 of 3 pages
INVENTOR(S) : J. Brion; A. Chollet; L. Demuynck; L, DeMontarby; Y. Rolland; J. Bonnet; P. Ghezzi, A. Fradin It is certified that error appears in the above-indentified patent and that said Letters Patent is hereby corrected as shown below:

Column 8, line 16 (approx.): "WΘ" should read -- W' --.

Column 8, line 25 (approx.): "WΘ" and "RΘ" should read -- W' -- and -- R'a --.

Column 8, line 42 (approx.): "$R_b'$" should read -- $R'_b$ --.

Column 8, line 55 (approx.): "$R_b'$" should read -- $R'_b$ --.

Column 8, line 63: "(x), (xzz), (xvzz), (xzxa)to (xzxe)or (xx)" should read: -- (X), (XII), (XVII), (XIXa) to (XIXe) or (XX) --.

Column 9, line 23(approx.): "$R_1'$" should read -- $R'_1$ -- .

Column 9, line 26(approx.): "$R_2'$" should read: -- $R'_2$ --.

Column 9, line 35(approx.): "$R_1'$" should read -- $R'_1$ --.

Column 9, line 38(approx.): "$R_2'$" should read: -- $R'_2$ --.

UNITED STATES PATENT AND TRADEMARK OFFICE
CERTIFICATE OF CORRECTION

PATENT NO. : 5,550,143
DATED : Aug. 27, 1996   Page 2 of 3
INVENTOR(S) : J. Brion; A. Chollet; L. Demuynck; L, DeMontarby; Y. Rolland; J. Bonnet; P. Ghezzi, A. Fradin It is certified that error appears in the above-indentified patent and that said Letters Patent is hereby corrected as shown below:

Column 9, line 61:  Delete the "o" at the end of the line.

Column 11, line 40:  "propyl" should read -- propyl] --.

Column 11, line 41:  Delete "]" from the beginning of the line.

Column 17, line 57(approx.):  After "Example 6" delete first occurrence of "5" (keeping the " dash").

Column 20, line 49:  Delete "groups".

Column 20, line 64:  Delete "from".

Column 21, line 37:  "to" at beginning of line should read -- or --.

Column 21, line 46 (approx.):  "$R_a'$" should read -- $R'_a$ --.

Column 22, line 3(approx.):  "$R_b'$" should read -- $R'_b$ --.

Column 22, line 44:  Insert a "-" (dash) between "pharmaceutically" and "acceptable".

UNITED STATES PATENT AND TRADEMARK OFFICE
CERTIFICATE OF CORRECTION

PATENT NO. : 5,550,143
DATED : Aug. 27, 1996
INVENTOR(S) : J. Brion; A. Chollet; L. Demuynck; L, DeMontarby; Y. Rolland; J. Bonnet; P. Ghezzi, A. Fradin It is certified that error appears in the above-indentified patent and that said Letters Patent is hereby corrected as shown below:

Column 22, line 50: "living body" should read -- mammal --.

Column 22, lines 58 & 59: Claim 4 should read -- A compound of claim 1 which is methyl 1-[3-(5-chloro-2-oxo-benzothiazolin-3-yl)-1-propyl]pyrrole-2-carboxylate. --.

Column 22, lines 60 & 61: Claim 5 should read -- A compound of claim 1 which is 5-chloro-3-[3-(8,8-dimethyl-1,3-dioxo-2-azaspiro [4.5]decan-2-yl) propyl] benzothiazolin-2-one. --

Signed and Sealed this

Tenth Day of December, 1996

Attest:

BRUCE LEHMAN

*Attesting Officer*   *Commissioner of Patents and Trademarks*